United States Patent
Ouchi et al.

(10) Patent No.: US 6,582,357 B2
(45) Date of Patent: Jun. 24, 2003

(54) TREATING INSTRUMENT ERECTING DEVICE FOR USE IN ENDOSCOPE

(75) Inventors: Naoya Ouchi, Saitama (JP); Shinichi Matsuno, Kanagawa (JP); Masahiro Takano, Tokyo (JP)

(73) Assignee: Pentax Corporation, Tokyo (JP)

( * ) Notice: Subject to any disclaimer, the term of this patent is extended or adjusted under 35 U.S.C. 154(b) by 168 days.

(21) Appl. No.: 09/840,134

(22) Filed: Apr. 24, 2001

(65) Prior Publication Data

US 2001/0044570 A1 Nov. 22, 2001

(30) Foreign Application Priority Data

| May 24, 2000 | (JP) | ..................................... 2000-152524 |
| Jul. 12, 2000 | (JP) | ..................................... 2000-210651 |
| Jan. 26, 2001 | (JP) | ..................................... 2001-018033 |

(51) Int. Cl.[7] ................................................ A61B 1/07
(52) U.S. Cl. ....................................... 600/107; 600/134
(58) Field of Search ................................. 600/107, 134

(56) References Cited

U.S. PATENT DOCUMENTS

| 5,112,330 A | * | 5/1992 | Nishigaki et al. ........... 600/143 |
| 5,170,775 A | * | 12/1992 | Tagami ....................... 356/241 |
| 5,460,168 A | * | 10/1995 | Masubuchi et al. ......... 600/123 |
| 5,562,600 A | | 10/1996 | Matsuno |
| 5,707,344 A | * | 1/1998 | Nakazawa et al. .......... 600/127 |
| 5,868,663 A | | 2/1999 | Katsurada et al. |
| 5,941,817 A | * | 8/1999 | Crawford .................... 600/134 |
| 6,001,058 A | * | 12/1999 | Sano et al. .................. 600/132 |

FOREIGN PATENT DOCUMENTS

| JP | 57-60601 | 9/1980 |
| JP | 62-90602 | 6/1987 |

* cited by examiner

*Primary Examiner*—John Fox
(74) *Attorney, Agent, or Firm*—Greenblum & Bernstein, P.L.C.

(57) ABSTRACT

A treating instrument erecting device for use in an endoscope includes a treating instrument erecting member for changing the direction of projection of the distal end portion of a treating instrument inserted in a treating instrument inserting channel. The treating instrument erecting member is provided at the distal end of an insert part of the endoscope. A control wire for operating the treating instrument erecting member is axially movably inserted in a wire guide provided in the insert part to extend over the entire length of the insert part. A wire driving member for advancing or retracting the control wire is provided in a control part connected to the proximal end of the insert part. The control wire and the wire driving member are electrically isolated from each other.

12 Claims, 15 Drawing Sheets

TREATING INSTRUMENT ERECTING DEVICE FOR USE IN ENDOSCOPE

BACKGROUND OF THE INVENTION

The present disclosure relates to subject matter contained in Japanese Patent Applications No. 2000-152524 (filed on May 24, 2000), No. 2000-210651 (filed on Jul. 12, 2000) and No. 2001-18033 (filed on Jan. 26, 2001), which are expressly incorporated herein by reference in their entireties.

1. Field of the Invention

The present invention relates to a treating instrument erecting device used in an endoscope to change the direction of projection of a treating instrument at will, which projects outwardly from the distal end of an insert part of the endoscope.

2. Description of the Prior Art

In general, a side-viewing endoscope or the like has a treating instrument erecting member provided at the distal end of an insert part thereof to change the direction of projection of the distal end portion of a treating instrument inserted in a treating instrument inserting channel. The treating instrument erecting member is operated by remote control from a control part connected to the proximal end of the insert part through a control wire inserted in the insert part.

When a treating instrument that is supplied with a high-frequency electric current is used in such an endoscope, if the high-frequency electric current leaks to the treating instrument erecting member, the leakage current may be conveyed to the control part. Therefore, there is a danger that the doctor holding the control part may get burnt when touching a metallic component provided in the control part, e.g. an erecting member control lever. Accordingly, the conventional practice is to use an electrically insulating material to form the surface of the treating instrument erecting member provided at the distal end of the insert part and the surfaces of components contacting the treating instrument erecting member.

However, the conventional structure using an electrically insulating material to form the surface of the treating instrument erecting member and the surfaces of the components contacting the treating instrument erecting member is not practical because such components using an electrically insulating material are readily breakable owing to the insufficient mechanical strength and the component machining process becomes complicated.

SUMMARY OF THE INVENTION

An object of the present invention is to provide a treating instrument erecting device for use in an endoscope that is capable of preventing the doctor from getting burnt when using a high-frequency treating instrument, with a structure of high practical utility.

Other objects and advantages of the present invention will become apparent from the following detailed description of illustrated embodiments of the invention.

According to the present invention, there is provided a treating instrument erecting device for use in an endoscope. The treating instrument erecting device includes a treating instrument erecting member for changing the direction of projection of the distal end portion of a treating instrument inserted in a treating instrument inserting channel. The treating instrument erecting member is provided at the distal end of an insert part of the endoscope. A control wire for operating the treating instrument erecting member is axially movably inserted in a wire guide provided in the insert part to extend over the entire length of the insert part. A wire driving member for advancing or retracting the control wire is provided in a control part connected to the proximal end of the insert part. The control wire and the wire driving member are electrically isolated from each other.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

A first embodiment of the present invention will be described below with reference to the accompanying drawings.

Figure 1:
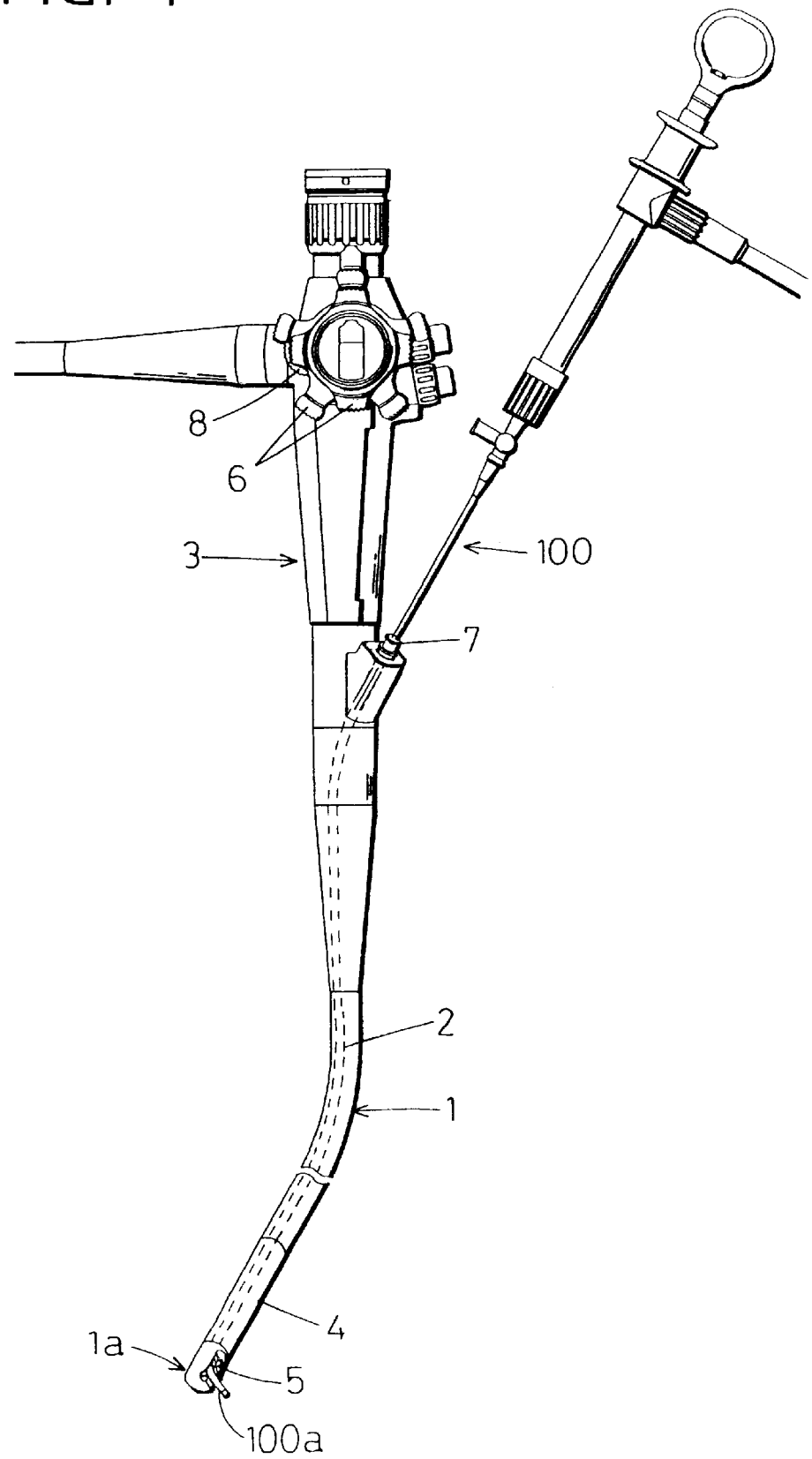
FIG. 1 is an external view showing the whole arrangement of an endoscope in a first embodiment of the present invention.

FIG. 1 shows an endoscope with a treating instrument 100 inserted therein. The endoscope has an insert part 1 covered with a flexible tube. A bendable portion 4 is formed at the distal end of the insert part 1. The bendable portion 4 can be bent as desired by remote control from a control part 3 connected to the proximal end of the insert part 1. Bending control knobs 6 are provided on the control part 3.

A treating instrument inserting channel 2 is inserted in the endoscope to extend throughout the insert part 1 and the bendable portion 4. The treating instrument inserting channel 2 is formed from an electrically insulating tubing material, for example, a tetrafluoroethylene resin tube. The proximal end of the treating instrument inserting channel 2 is connected to a treating instrument inlet 7 provided to project from a portion in the vicinity of the joint between the insert part 1 and the control part 3. The distal end of the treating instrument inserting channel 2 is positioned in a distal end portion 1a of the insert part 1.

Various treating instruments 100 may be inserted into the treating instrument inserting channel 2. In this embodiment, the treating instrument inserting channel 2 has a high-frequency treating instrument inserted therein to perform a treatment with a high-frequency electric current passed therethrough.

A distal end portion 100a of the treating instrument 100 projects sideward from the distal end portion 1a of the insert part 1. A treating instrument erecting member 5 is provided in the distal end portion 1a of the insert part 1 to change the direction of projection of the distal end portion 100a of the treating instrument 100. The treating instrument erecting member 5 is pivotally operated with a control wire that is driven to advance or retract with an erecting member control knob 8 provided on the control part 3.

Figure 2:
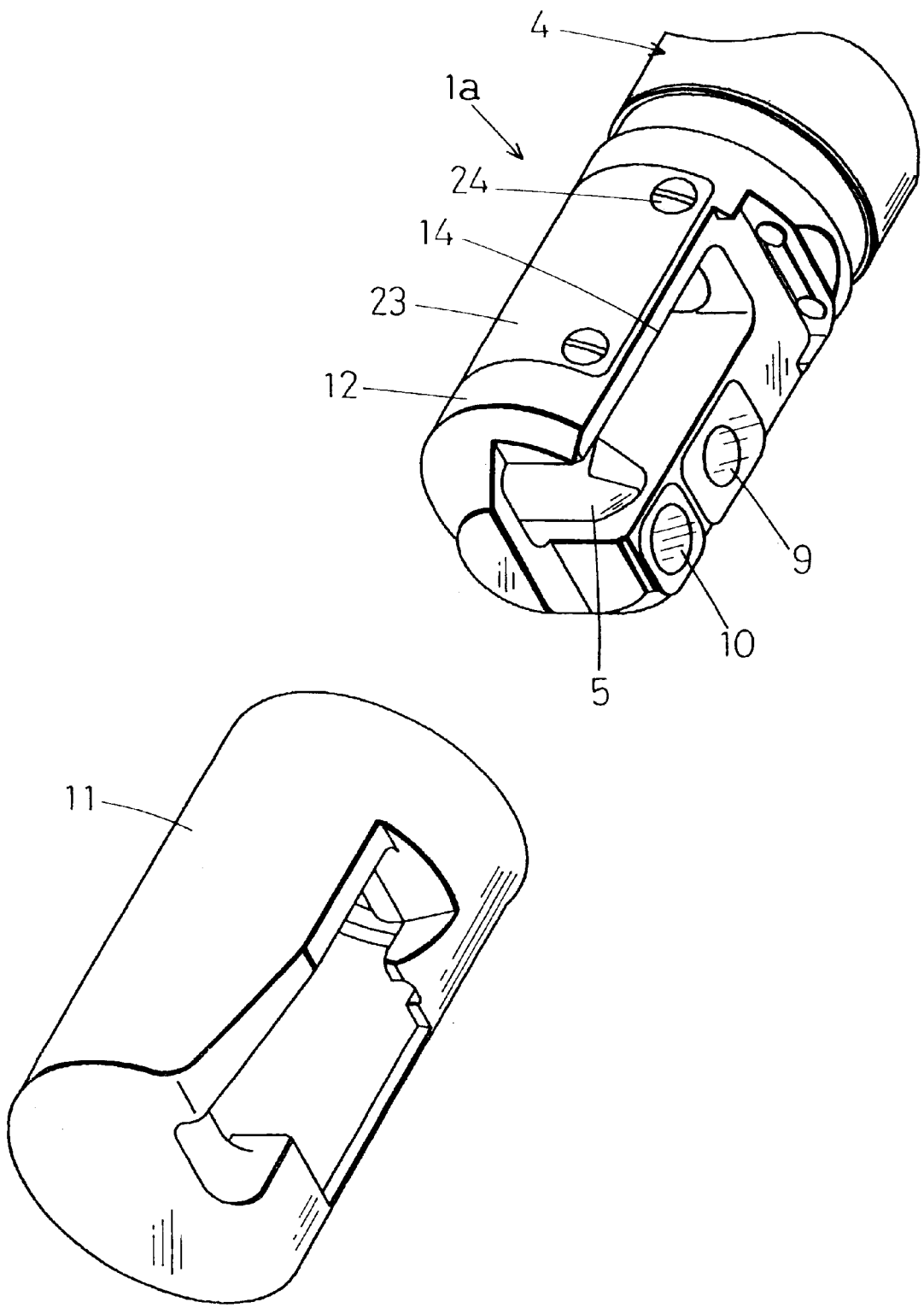
FIG. 2 is an exploded perspective view showing a distal end portion of an insert part of the endoscope in the first embodiment of the present invention.

FIG. 2 is an exploded perspective view of the distal end portion 1a of the insert part 1, showing a state where an electrically insulating cap 11 is detached from a distal end block 12. The distal end block 12 is made of a stainless steel. A viewing window 9, an illuminating window 10 and a treating instrument guide groove 14 are provided on the outer peripheral surface of the distal end block 12. An electrically insulating cap 11 covers the distal end block 12, exclusive of the viewing window 9, the illuminating window 10 and the opening of the treating instrument guide groove 14. The electrically insulating cap 11 is formed from a fluororubber or plastic material, for example.

Because the endoscope in this embodiment is a side-viewing endoscope, the viewing window 9 and the illuminating window 10 are provided on a side surface of the distal end block 12. The treating instrument erecting member 5 is installed in the treating instrument guide groove 14 formed in side-by-side relation to the viewing window 9 and the illuminating window 10.

Figure 3:
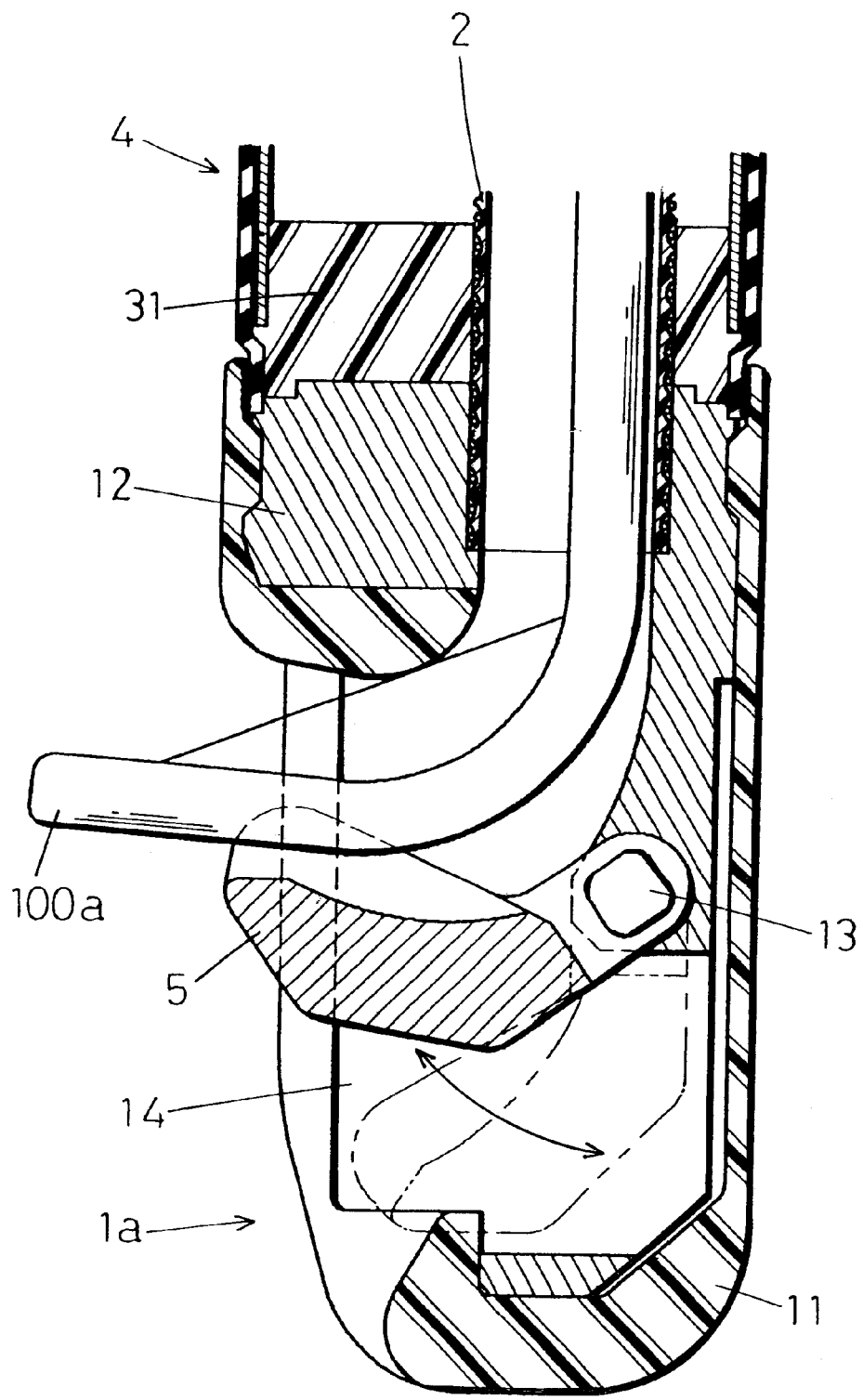
FIG. 3 is a sectional side view showing the distal end portion of the insert part of the endoscope in the first embodiment of the present invention.
Figure 4:
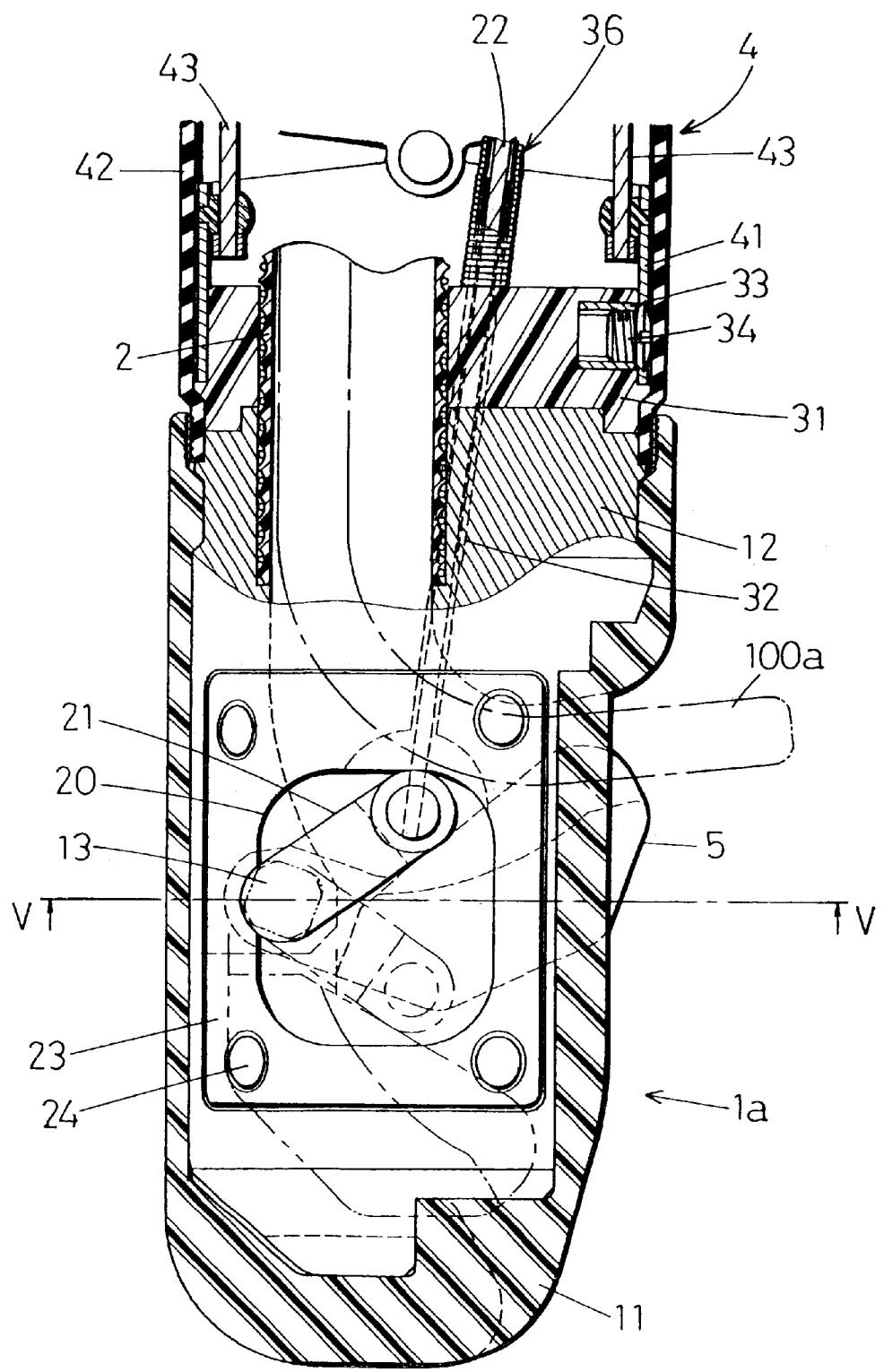
FIG. 4 is a composite sectional side view showing the distal end portion of the insert part of the endoscope in the first embodiment of the present invention.
Figure 5:
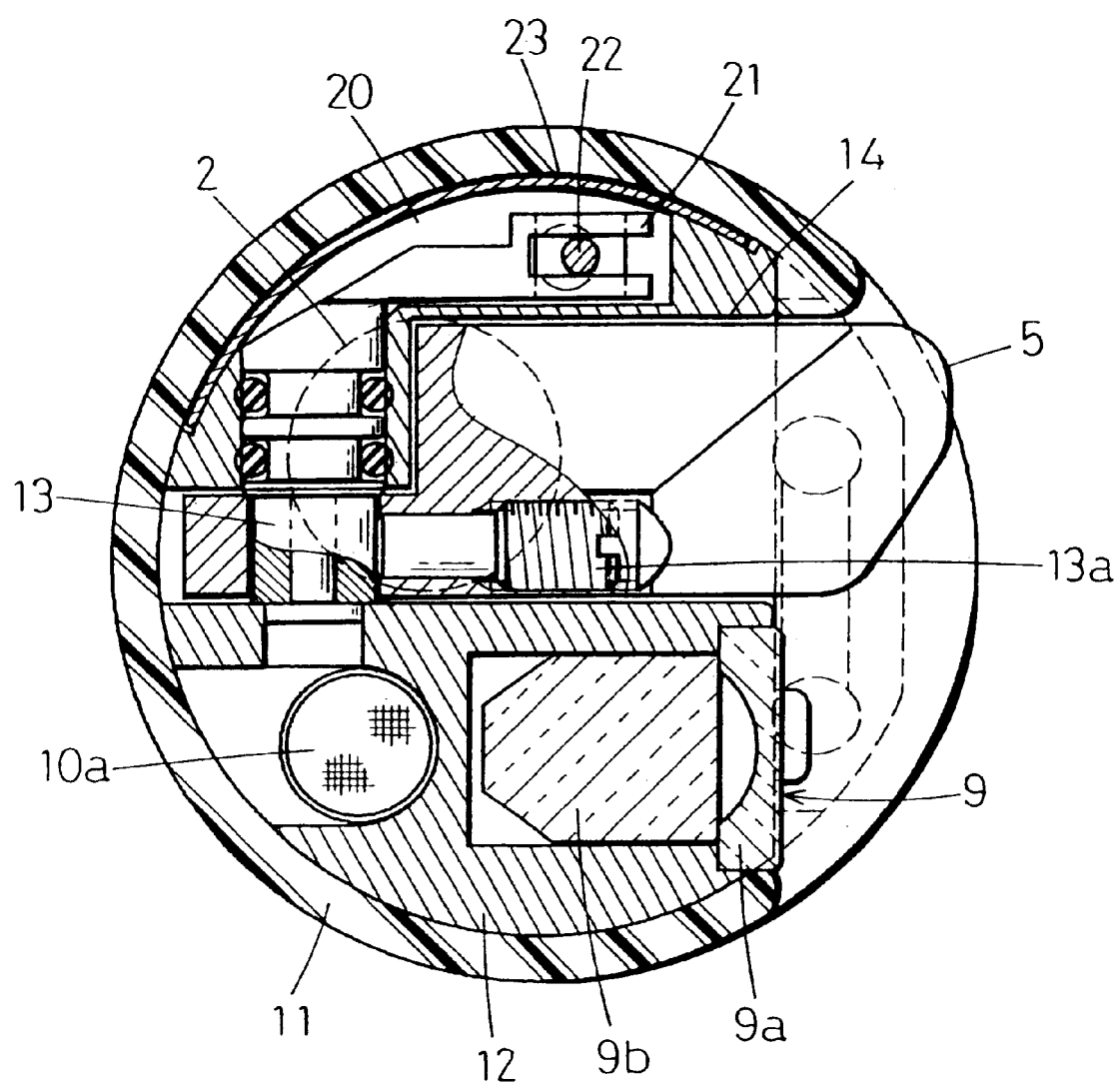
FIG. 5 is a sectional view taken along the line V—V in FIG. 4, showing the first embodiment of the present invention.

FIG. 3 is a sectional side view of the distal end portion 1a of the insert part 1, which is taken along the center plane of the treating instrument guide groove 14. FIG. 4 is a composite sectional side view (containing a plurality of sections taken along different planes) of the distal end portion 1a of the insert part 1 as seen from a direction opposite to the viewing direction of FIG. 3. FIG. 5 is a sectional view taken along the line V—V in FIG. 4.

As shown in FIG. 5, a cover lens 9a is attached to the distal end block 12 to cover the viewing window 9. A right-angled roof prism 9b is positioned inside the cover lens 9a. A light guide fiber bundle 10a is provided in such a manner that an exit end surface thereof is located inside the illuminating window 10.

The treating instrument erecting member 5 is disposed in the treating instrument guide groove 14 with a predetermined width formed in the distal end block 12 alongside of the viewing window 9 and the illuminating window 10. As shown in FIG. 3, the treating instrument erecting member 5 is capable of pivoting about an erecting member driving shaft 13.

The distal end of the treating instrument inserting channel 2 is communicably connected to the inner portion of the treating instrument guide groove 14. It should be noted that the treating instrument erecting member 5 is formed as a metallic monolithic component of a stainless steel or the like. Accordingly, the treating instrument erecting member 5 is excellent in mechanical strength and easy to manufacture.

As shown in FIGS. 4 and 5, an erecting member driving chamber 20 is defined by a recess formed in the outer surface of the outer wall of a pair of side walls of the distal end block 12 that face each other across the treating instrument guide groove 14. The erecting member driving chamber 20 accommodates an erecting member driving lever 21 integrally connected to the erecting member driving shaft 13 at right angles thereto.

A thin metal sheet 23 covers a side opening of the erecting member driving chamber 20. As shown in FIG. 2, the thin metal sheet 23 is secured to the distal end block 12 with four screws 24. It should be noted that the erecting member driving lever 21 and the erecting member driving shaft 13 are also made of a stainless steel.

A control wire 22 is a single stranded wire formed by twisting together thin stainless steel wires. The outer surface of the control wire 22 is coated with an electrically insulating material, for example, a tetrafluoroethylene resin material or a polyamide resin material.

As shown in FIG. 4, the control wire 22 extends through a guide hole 32 formed in the distal end block 12. The guide hole 32 opens into the erecting member driving chamber 20 from the rear side. The distal end of the control wire 22 is connected to an end portion of the erecting member driving lever 21 in the erecting member driving chamber 20.

The erecting member driving shaft 13 and the treating instrument erecting member 5 are connected together by the fit between a square shaft and a square hole so as not to rotate relative to each other, and secured to each other with a fixing screw 13a, as shown in FIG. 5.

With the above-described structure, when the erecting member driving lever 21 pivots about the erecting member driving shaft 13 in response to the advancing or retracting motion of the control wire 22, the pivoting motion is transmitted to the treating instrument erecting member 5 through the erecting member driving shaft 13 as it is. Consequently, the treating instrument erecting member 5 pivots about the erecting member driving shaft 13 to change the direction of projection of the distal end portion 100a of the treating instrument 100 inserted in the treating instrument inserting channel 2.

As shown in FIG. 4, the distal end portion 1a of the insert part 1 arranged as stated above is connected to the distal end part of the bendable portion 4. The bendable portion 4 is formed by rotatably connecting together a large number of joint rings. In the figure, the foremost joint ring 41 is shown. Reference numeral 42 denotes a skin rubber tube. Reference numeral 43 denotes a bending control wire.

The metallic distal end block 12 is not directly connected to the foremost joint ring 41 of the bendable portion 4, but instead the foremost joint ring 41 is fitted to an electrically insulating block 31 secured to the rear end portion of the distal end block 12 with an adhesive or the like. In this state, the foremost joint ring 41 is screwed to the electrically insulating block 31.

The electrically insulating block 31 is formed from an electrically insulating material such as a plastic material, e.g. polycarbonate, or a ceramic material. A machine screw 34 for securing the foremost joint ring 41 is screwed into a metallic collar 33 embedded in the electrically insulating block 31.

Accordingly, the members constituting the bendable portion 4 and the distal end block 12 are completely electrically isolated from each other. If a high-frequency electric current leaks to the treating instrument erecting member 5, which is a metallic monolithic component, the leakage current cannot be conveyed to the bendable portion 4.

Figure 6:
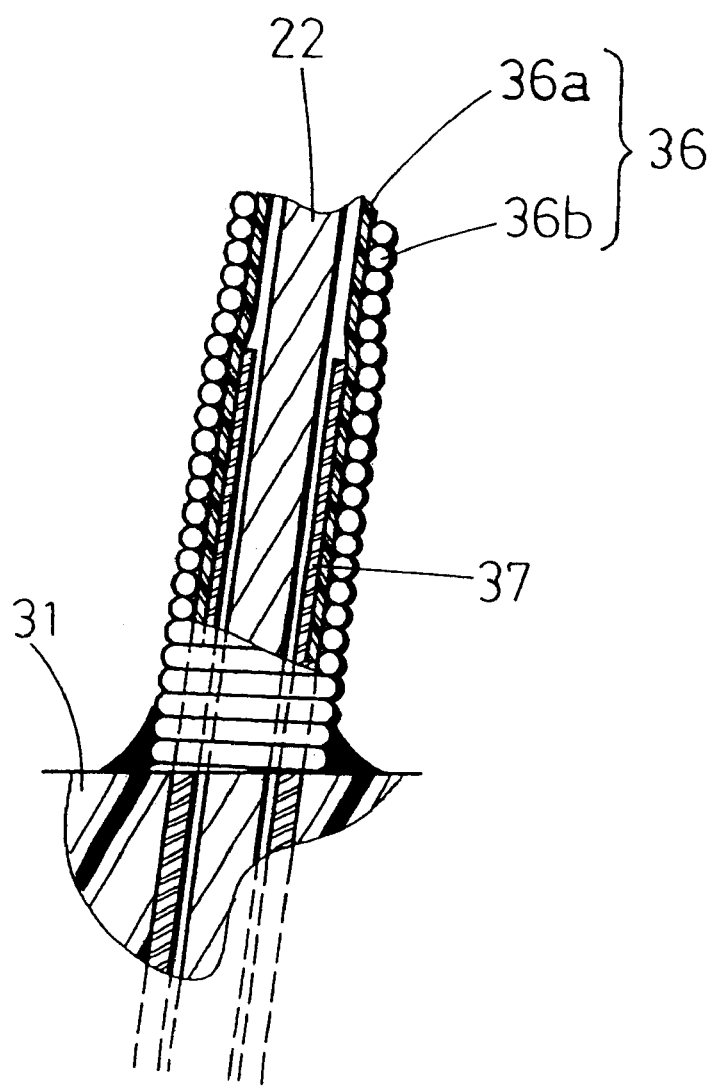
FIG. 6 is an enlarged sectional view showing a secured portion at the distal end of a wire guide in the first embodiment of the present invention.

The control wire 22 is axially movably inserted in a wire guide 36 provided in the insert part 1. The wire guide 36 extends over the entire length of the insert part 1, inclusive of the bendable portion 4. FIG. 6 shows a distal end portion of the wire guide 36 that is secured to the electrically insulating block 31.

The wire guide 36 is formed from an electrically insulating tube 36a of a tetrafluoroethylene resin material, for example. The electrically insulating tube 36a is inserted in a coil pipe 36b over the entire length thereof. The coil pipe 36b is formed by close-winding a stainless steel wire with a uniform diameter. Accordingly, if a high-frequency electric current leaks to the control wire 22, the leakage current cannot be conveyed to the wire guide 36.

The distal end portion of the wire guide 36 is secured to one end portion of a non-metallic (electrically insulating) connecting pipe 37 by bonding. The connecting pipe 37 extends through the electrically insulating block 31, and the other end of the connecting pipe 37 is secured to the metallic distal end block 12.

Figure 7:
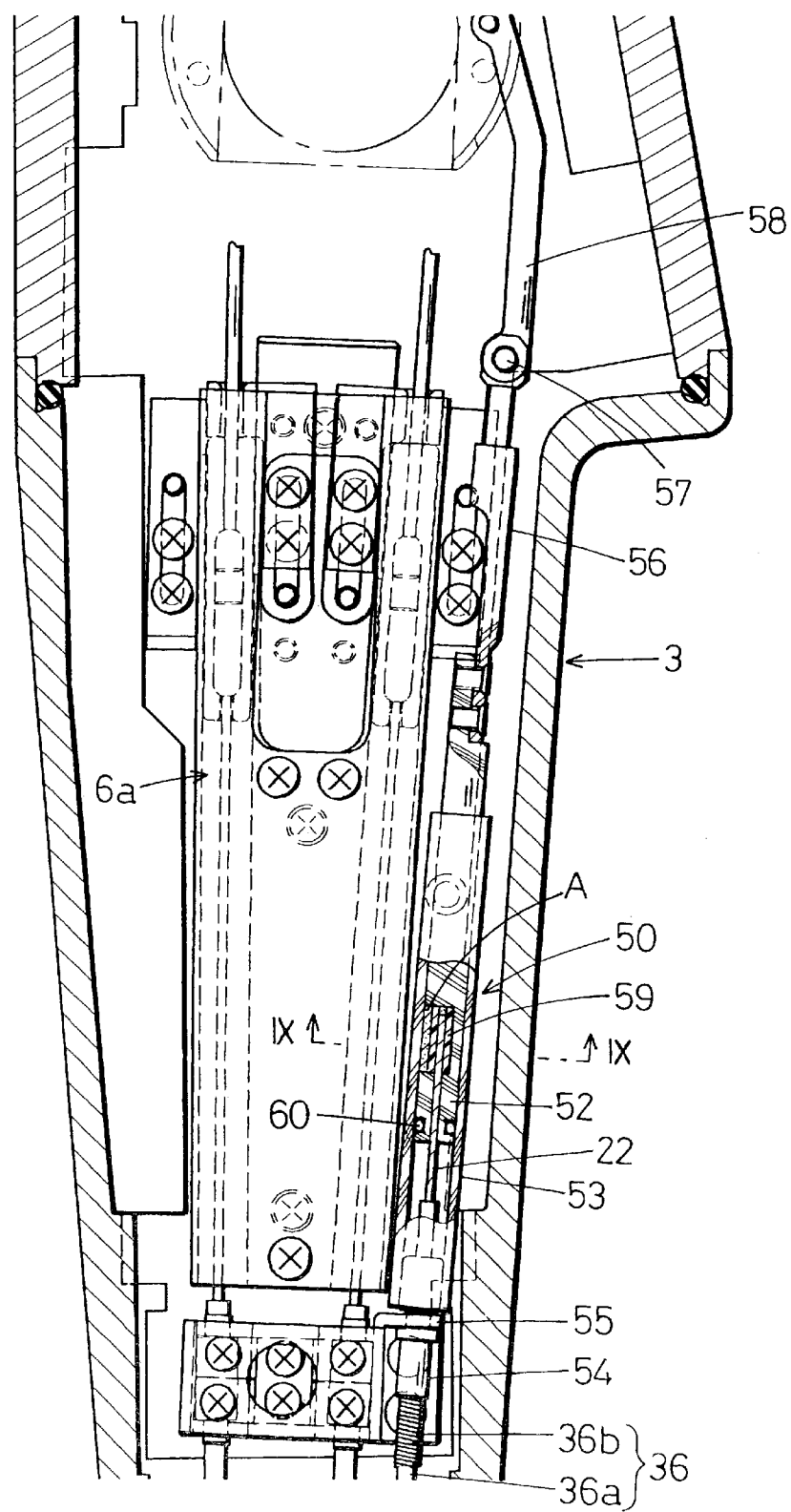
FIG. 7 is a partly-sectioned front view showing the internal structure of a control part of the endoscope in the first embodiment of the present invention.

FIG. 7 shows the internal structure of the control part 3. A bending control mechanism 6a is actuated with the bending control knobs 6 to advance or retract the above-described bending control wire 43. An erecting member driving mechanism 50 is positioned along the bending control mechanism 6a. The erecting member driving mechanism 50 is actuated with the erecting member control knob 8.

Figure 8:
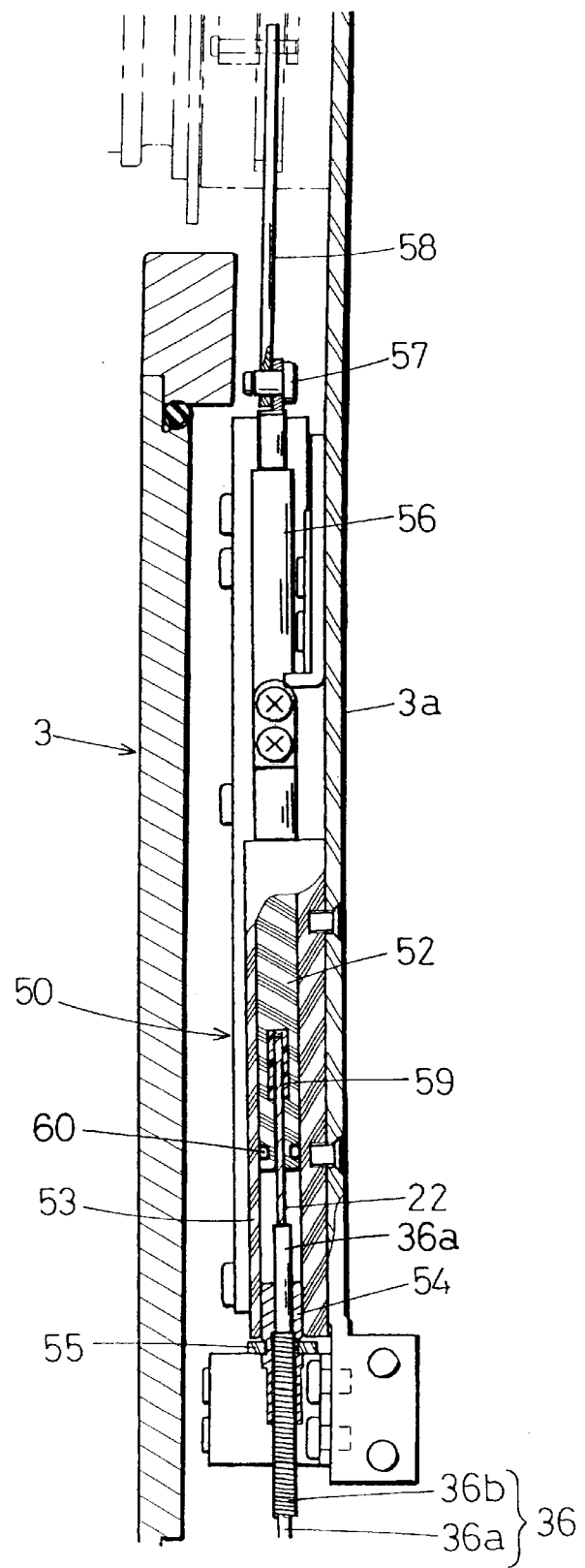
FIG. 8 is a partly-sectioned side view showing the internal structure of the control part of the endoscope in the first embodiment of the present invention.

FIG. 7 is a partly-sectioned front view of the erecting member driving mechanism 50. FIG. 8 is a partly-sectioned side view of the erecting member driving mechanism 50. In the figures, a guide tube 53 is formed from a metal pipe material or the like. The guide tube 53 is screwed to a frame 3a in the control part 3.

A wire driving rod 52 made of a metal rod material is axially movably provided in the guide tube 53. A tubular stopper 59 is secured to the proximal end of the control wire 22 drawn out of the proximal end of the wire guide 36. An O-ring 60 made of a rubber material is fitted on the wire driving rod 52 so as to produce sliding resistance against the advancing or retracting motion of the wire driving rod 52 relative to the guide tube 53.

The tubular stopper 59 is formed in a tubular shape from an electrically insulating plastic material, e.g. a tetrafluoroethylene resin material or a polyamide resin material. The proximal end portion of the control wire 22 is inserted into the tubular stopper 59 until the proximal end surface of the control wire 22 enters the tubular stopper 59 to some extent. That is, some space is left at the rear of the proximal end surface of the control wire 22 in the tubular stopper 59. In this state, the control wire 22 and the tubular stopper 59 are firmly joined together.

Figure 9:
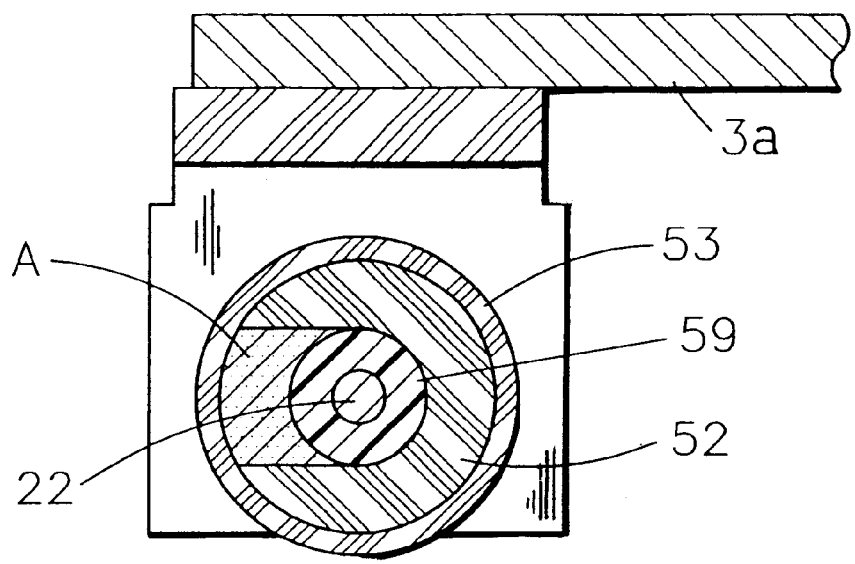
FIG. 9 is a sectional view taken along the line IX—IX in FIG. 7, showing the first embodiment of the present invention.

FIG. 9 is a sectional view taken along the line IX—IX in FIG. 7. As shown in FIG. 9, the tubular stopper 59 is fitted in a groove formed in the wire driving rod 52. The control wire 22 is drawn out to extend forwardly from a hole formed at the central axis position in the wire driving rod 52.

With the above-described arrangement, the control wire 22 is fixedly connected to the wire driving rod 52 in an electrically isolated manner. It should be noted, as shown in FIGS. 7 and 9, that the space remaining in the groove of the wire driving rod 52 after the tubular stopper 59 has been fitted therein is filled with an electrically insulating adhesive A to prevent the tubular stopper 59 from becoming loose.

As shown in FIGS. 7 and 8, a connecting pipe 56 is connected to the other end of the wire driving rod 52 with screws, and a link 58 is rotatably connected to the connecting pipe 56 through a pin 57. The link 58 is driven by the erecting member control knob 8.

A metallic stopper 54 is secured to the proximal end of the coil pipe 36b of the wire guide 36 by soldering, for example. The stopper 54 is retained by a support member 55 secured to the frame 3a.

The end of the electrically insulating tube 36a of the wire guide 36 projects a predetermined length (e.g. from several millimeters to several centimeters) from the end of the coil pipe 36b to ensure electrical isolation between the control wire 22 and the stopper 54 and other metallic components in the control part 3.

With the above-described structure, when the erecting member control knob 8 is actuated, the control wire 22 advances or retracts in the wire guide 36 through the erecting member driving mechanism 50. In response to the advancing or retracting motion of the control wire 22, the treating instrument erecting member 5 provided in the distal end portion 1a pivots to change the direction of projection of the distal end portion 100a of the treating instrument 100.

Because the control wire 22 is electrically isolated from the erecting member driving mechanism 50 provided in the control part 3 and the wire guide 36, if a high-frequency electric current leaks to the treating instrument erecting member 5 when a high-frequency treating instrument is used as the treating instrument 100, the leakage current cannot be conveyed to any of the metallic components in the control part 3. Therefore, there is no danger that the doctor holding the control part 3 may have a burn.

It should be noted that the surface of the coil pipe 36b of the wire guide 36 may also be subjected to an electrically insulating treatment, e.g. electrically insulating coating, to ensure electrical isolation even more surely.

FIGS. 10 to 14 show a second embodiment of the present invention. In the second embodiment, members identical or similar to those in the first embodiment are denoted by the same reference numerals as those used in the first embodiment, and a description of the same members as those in the first embodiment is omitted appropriately.

Figure 10:
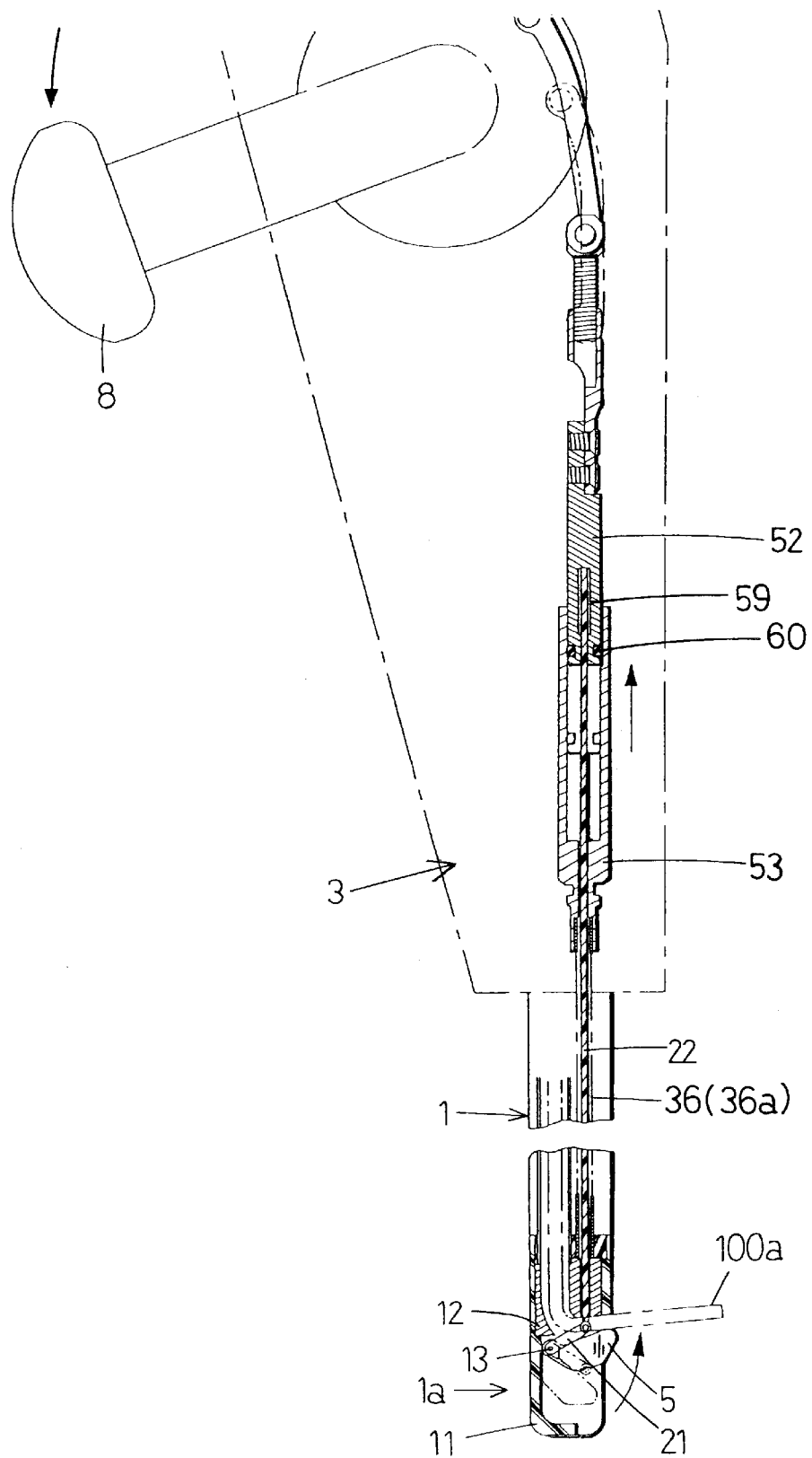
FIG. 10 is a schematic view showing the whole arrangement of a treating instrument erecting device according to a second embodiment of the present invention.
Figure 11:
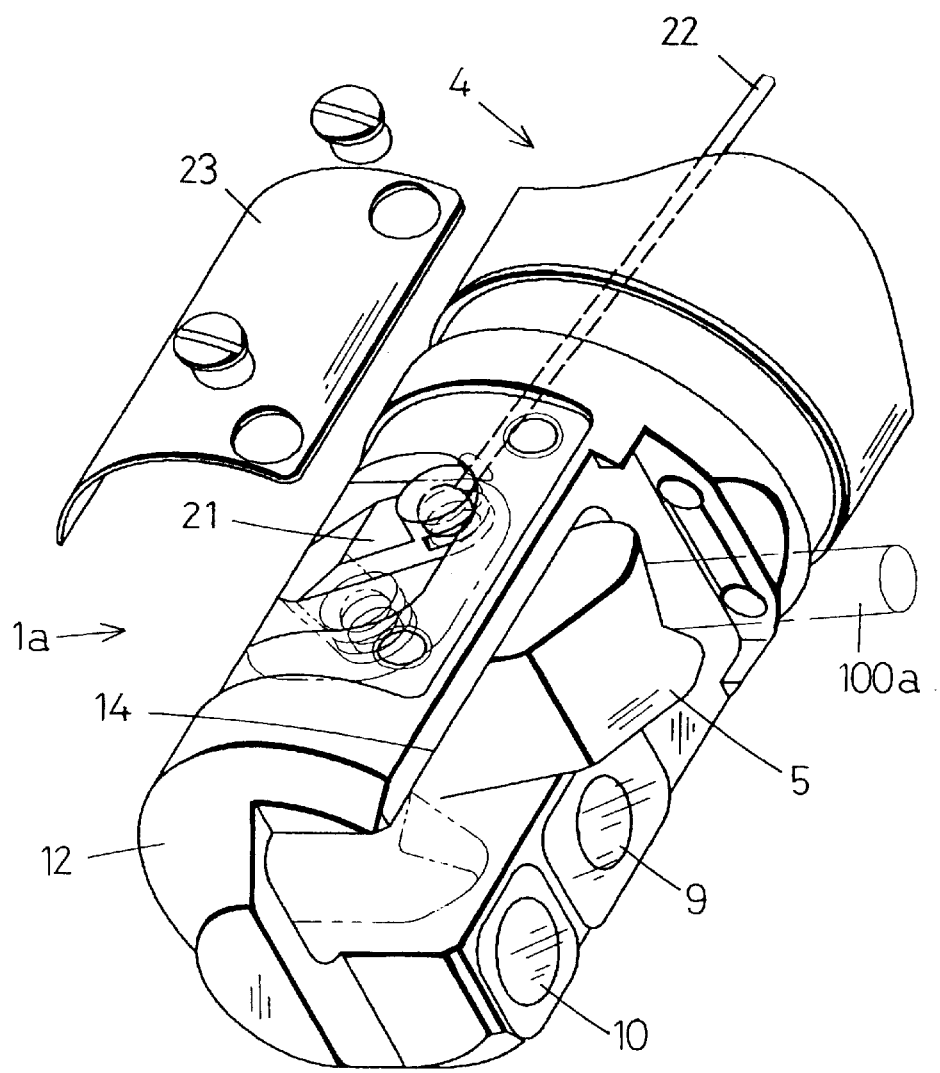
FIG. 11 is an exploded perspective view showing a distal end portion of an insert part of an endoscope in the second embodiment of the present invention.
Figure 12:
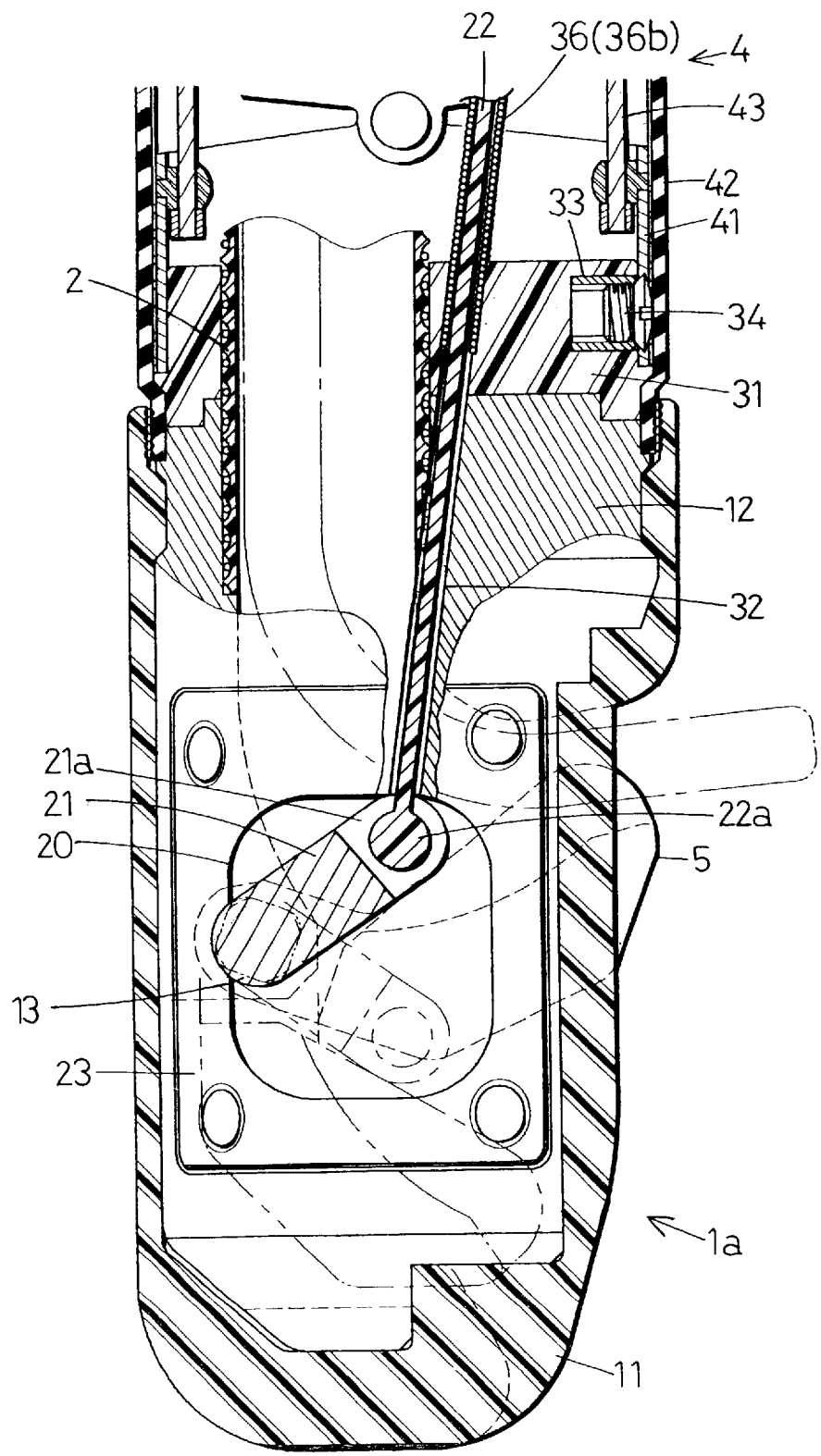
FIG. 12 is a composite sectional side view showing the distal end portion of the insert part of the endoscope in the second embodiment of the present invention.

FIG. 10 is a schematic view showing the whole arrangement of a treating instrument erecting device for driving the treating instrument erecting member 5 according to the second embodiment of the present invention. FIG. 11 is an exploded perspective view of the distal end portion 1a of the insert part 1. FIG. 12 is a composite sectional side view of the distal end portion 1a of the insert part 1, which is taken along the center plane of the treating instrument guide groove 14.

In this embodiment, the control wire 22 for erecting a treating instrument is formed from a plastic material having electrical insulating properties and high tensile strength as well as flexibility, e.g. a polyester resin material. Accordingly, the treating instrument erecting control wire 22 cannot act as a medium conducting a high-frequency electric current.

Figure 13:
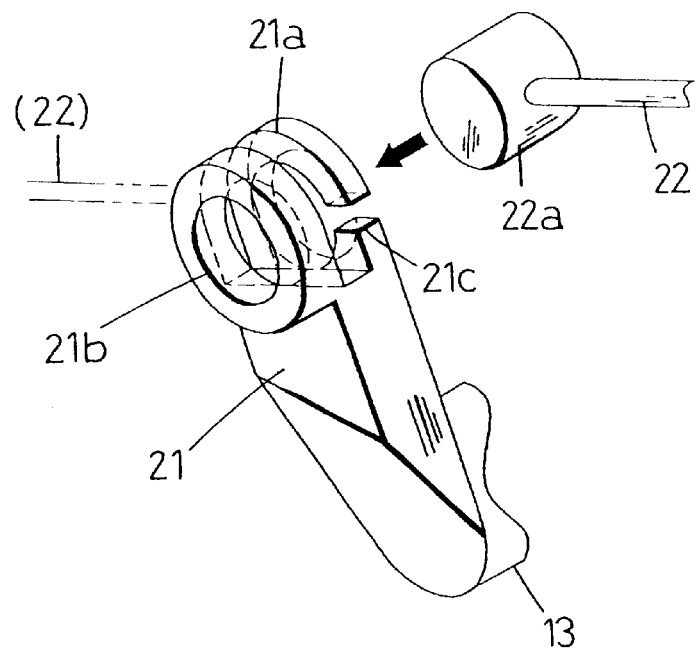
FIG. 13 is an exploded perspective view showing the joint between a treating instrument erecting control wire and a treating instrument erecting member in the second embodiment of the present invention.

As shown in FIGS. 12 and 13, the distal end portion 22a of the treating instrument erecting control wire 22 is thermoformed in the shape of a columnar knob extending perpendicularly to the axis of the treating instrument erecting control wire 22. The knob-shaped distal end portion 22a is rotatably fitted in an engagement hole 21b formed in the erecting member driving lever 21. Thus, the treating instrument erecting control wire 22 is connected to the erecting member driving lever 21 in such a manner as to pass through a slot 21a formed in the erecting member driving lever 21.

Figure 14:
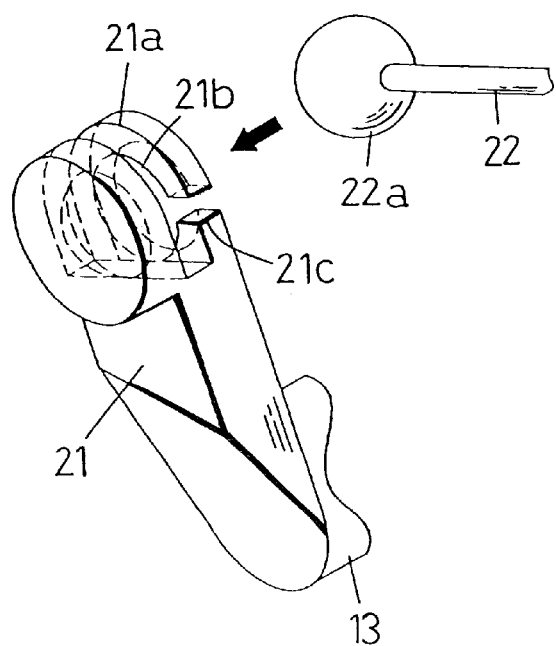
FIG. 14 is an exploded perspective view showing another example of the joint between the treating instrument erecting control wire and the treating instrument erecting member in the second embodiment of the present invention.

As shown in FIG. 13, a slit 21c is formed in the erecting member driving lever 21 to allow the treating instrument erecting control wire 22 to pass during assembly. After the assembly, the treating instrument erecting control wire 22 is drawn out to extend from a side of the erecting member driving lever 21 reverse to the slit 21c as shown by the chain double-dashed line. In this state, the treating instrument erecting control wire 22 is used in the treating instrument erecting device. Thus, the knob-shaped distal end portion 22a prevents the treating instrument erecting control wire 22 from dislodging from the erecting member driving lever 21. It should be noted that the knob-shaped distal end portion 22a of the treating instrument erecting control wire 22 may be formed in other shapes, for example, a spherical shape as shown in FIG. 14.

Thus, the knob-shaped distal end portion 22a of the treating instrument erecting control wire 22 is connected to the erecting member driving lever 21 in such a manner as to be rotatable about the axis of the engagement hole 21b. Accordingly, when the treating instrument erecting control wire 22 is advanced or retracted by actuating the erecting member control knob 8, the erecting member driving lever 21 pivots about the erecting member driving shaft 13, thereby making it possible to change the direction of projection of the distal end portion 100a of the treating instrument 100 inserted in the treating instrument inserting channel 2.

The above-described arrangement allows the treating instrument erecting member 5 to be driven to pivot in a state where the treating instrument erecting control wire 22 is electrically isolated from the distal end block 12 and the treating instrument erecting member 5. Therefore, if a high-frequency electric current leaks from the treating instrument 100 to the treating instrument erecting member 5 or the distal end block 12, the leakage current cannot be conveyed from the distal end block 12 to the control part 3 through the treating instrument erecting control wire 22.

It should be noted that in this embodiment the treating instrument erecting control wire 22 per se has no electrical conductivity, as stated above. Therefore, the wire guide 36 is formed from only the coil pipe 36b formed by close-winding a stainless steel wire.

Furthermore, the tubular stopper for connecting the treating instrument erecting control wire 22 to the wire driving rod 52 in the control part 3 may be made of a metallic material in place of a plastic material as used in the first embodiment.

Figure 15:
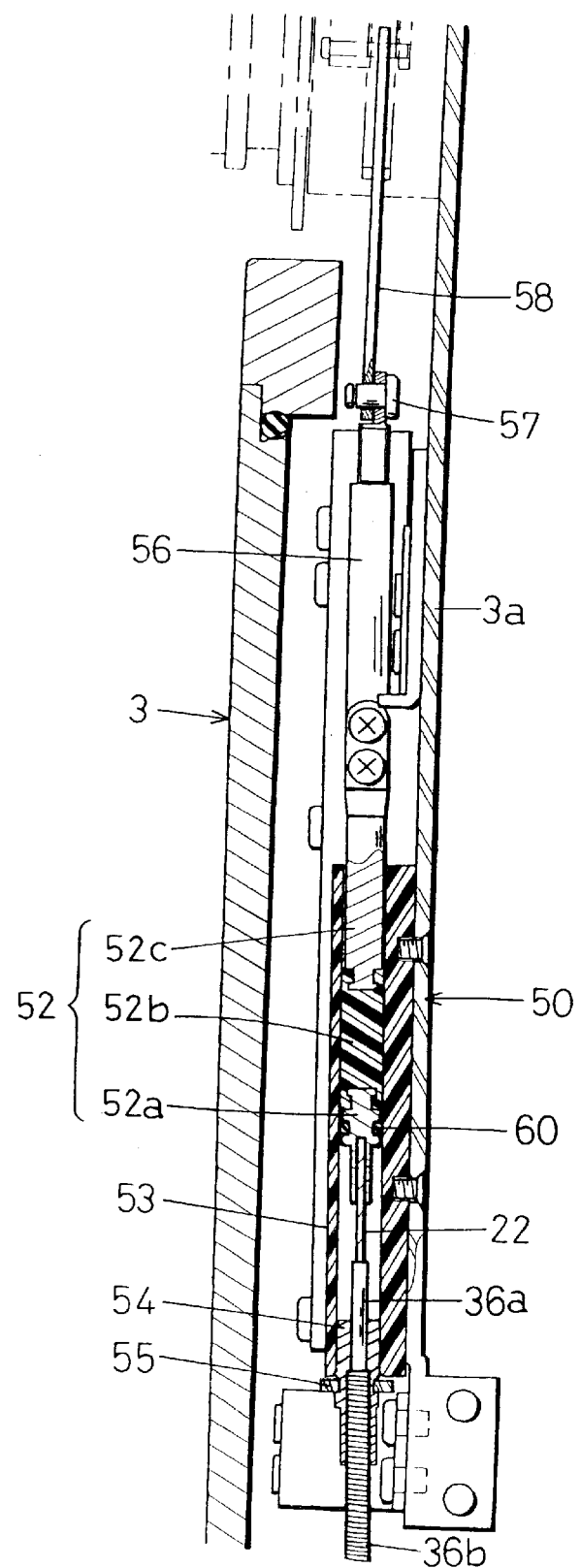
FIG. 15 is a partly-sectioned side view showing the internal structure of a control part of an endoscope in a third embodiment of the present invention.
Figure 16:
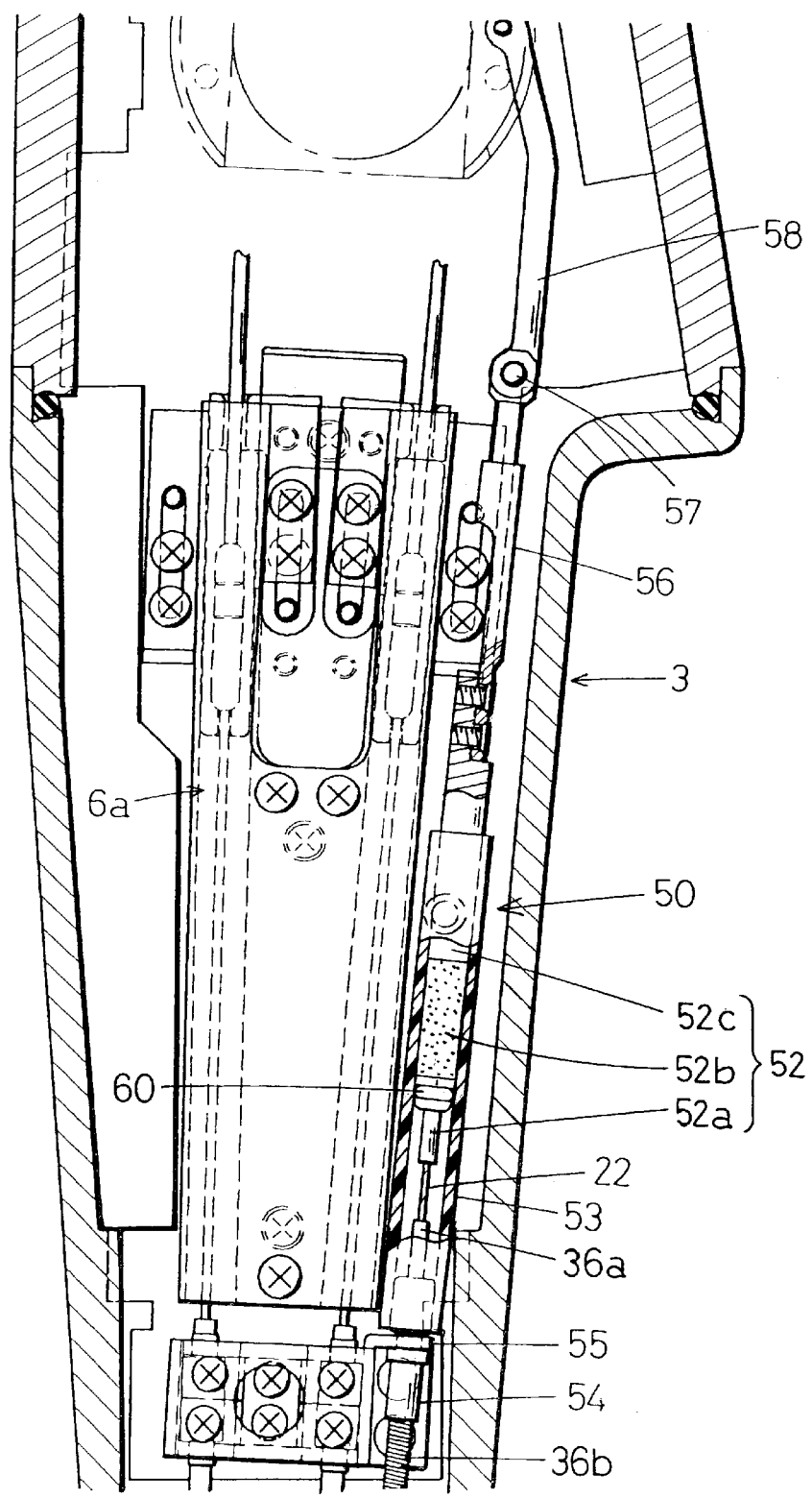
FIG. 16 is a partly-sectioned front view showing the internal structure of the control part of the endoscope in the third embodiment of the present invention.

FIGS. 15 and 16 show the erecting member driving mechanism 50 in the control part 3 according to a third embodiment of the present invention. In this embodiment, the control wire 22 is formed from an electrically conductive wire, e.g. a stainless steel wire, and the outer surface of the control wire 22 is not subjected to an electrically insulating treatment such as electrically insulating coating.

The wire guide 36 is formed from an electrically insulating tube 36a inserted in a coil pipe 36b formed by close-winding a stainless steel wire with a uniform diameter as in the case of the first embodiment.

The wire driving rod 52 has a distal metallic portion 52a firmly connected to the proximal end of the control wire 22 by soldering or the like. The wire driving rod 52 further has a proximal metallic portion 52c connected to the connecting pipe 56 (described later) with screws at the proximal end of the wire driving rod 52. The distal and proximal metallic portions 52a and 52c are disposed to face each other across an intermediate insulating portion 52b made of a rigid plastic material or the like having electrical insulating properties. The distal metallic portion 52a, the intermediate insulating portion 52b and the proximal metallic portion 52c are integrally joined together with an adhesive, for example.

The intermediate insulating portion 52b is formed with a length sufficient to ensure electrical isolation between the distal and proximal metallic portions 52a and 52c so that even if a high-frequency electric current flows through the distal metallic portion 52a, the influence of the current is not exerted upon the proximal metallic portion 52c.

In addition, the guide tube 53 surrounding the exposed portion of the control wire 22 drawn out of the wire guide 36 is formed from a rigid plastic material or the like having electrical insulating properties to ensure electrical isolation between the exposed portion of the control wire 22 and the surroundings.

Thus, electrical isolation is provided between the control wire 22 and the erecting member driving mechanism 50 provided in the control part 3. Therefore, if a high-frequency electric current leaks to the treating instrument erecting member 5 when a high-frequency treating instrument is used as the treating instrument 100, there is no danger that the doctor holding the control part 3 may have a burn.

According to the present invention, if there is leakage of a high-frequency electric current at the distal end of the insert part, the leakage current cannot be conveyed to the control part. Therefore, there is no danger that the doctor or assistant holding the control part may get burnt with the leakage current. In addition, all members that require mechanical strength, such as the treating instrument erecting member provided at the distal end of the insert part and the surrounding components, can be formed from metallic components. Therefore, there is no problem in terms of mechanical strength, and the components are easy to manufacture. Thus, the treating instrument erecting device according to the present invention has high practical utility.

While the invention has been described by reference to specific embodiments chosen for purposes of illustration, it should be apparent that numerous modifications could be made thereto by those skilled in the art without departing from the basic concept and scope of the invention.

What is claimed is:

1. A treating instrument erecting device for use in an endoscope, comprising:
   a treating instrument erecting member for changing a direction of projection of a distal end portion of a treating instrument inserted in a treating instrument inserting channel, said treating instrument erecting member being provided at a distal end of an insert part of said endoscope;
   a control wire for operating said treating instrument erecting member, said control wire being axially movably inserted in a wire guide provided in said insert part to extend over an entire length of said insert part; and a wire driving member for advancing or retracting said control wire, said wire driving member being provided in a control part connected to a proximal end of said insert part;

wherein said control wire and said wire driving member are electrically isolated from each other.

2. A treating instrument erecting device according to claim 1, wherein said control wire is covered with an electrically insulating coating over an entire length thereof.

3. A treating instrument erecting device according to claim 2, wherein said control wire and said wire driving member are connected together by fitting an electrically insulating tubular stopper to said wire driving member, said tubular stopper being secured to a proximal end portion of said control wire.

4. A treating instrument erecting device according to claim 3, wherein an electrically insulating tube is provided inside said wire guide to provide electrical isolation between said wire guide and said control wire.

5. A treating instrument erecting device according to claim 4, wherein an outer surface of said wire guide has been subjected to an electrically insulating treatment.

6. A treating instrument erecting device according to claim 1, wherein said control wire is formed from an electrically insulating material.

7. A treating instrument erecting device according to claim 6, wherein said control wire is formed from a plastic material.

8. A treating instrument erecting device according to claim 7, wherein said plastic material is a polyester resin material.

9. A treating instrument erecting device according to claim 7, wherein a distal end of the plastic material forming said control wire is formed in a knob-like shape to prevent said control wire from dislodging from a member to which said control wire is connected.

10. A treating instrument erecting device according to claim 1, wherein a joint between said control wire and said wire driving member is formed from an electrically insulating material.

11. A treating instrument erecting device according to claim 10, wherein among components constituting said wire driving member, a component connected directly to said control wire is a metallic component, and a component connected to said metallic component is made of an electrically insulating material.

12. A treating instrument erecting device according to claim 10, wherein a member surrounding an exposed portion of said control wire drawn out of said wire guide in said control part is formed from an electrically insulating material.

* * * * *